United States Patent [19]
Lang et al.

[11] Patent Number: 6,077,224
[45] Date of Patent: Jun. 20, 2000

[54] METHODS AND DEVICE FOR IMPROVING BROADBAND ULTRASONIC ATTENUATION AND SPEED OF SOUND MEASUREMENTS USING ANATOMICAL LANDMARKS

[76] Inventors: Philipp Lang, 225 Lincoln Way #206, San Francisco, Calif. 64122; John D. Mendlein, 680 Neptune Ave., Encinitas, Calif. 92024

[21] Appl. No.: 09/046,324

[22] Filed: Mar. 23, 1998

[51] Int. Cl.[7] ........................................ A61B 8/00
[52] U.S. Cl. ................................ 600/437; 600/449
[58] Field of Search ........................... 600/437, 442, 600/449; 601/2; 73/597, 599

[56] References Cited

U.S. PATENT DOCUMENTS

| | | |
|---|---|---|
| 3,648,685 | 3/1972 | Hepp et al. . |
| 3,713,329 | 1/1973 | Munger . |
| 3,782,177 | 1/1974 | Hoop . |
| 3,847,141 | 11/1974 | Hoop . |
| 4,043,181 | 8/1977 | Nigam . |
| 4,048,986 | 9/1977 | Ott . |
| 4,056,970 | 11/1977 | Sollish . |
| 4,217,912 | 8/1980 | Hubmann et al. . |
| 4,224,829 | 9/1980 | Kawabuchi et al. . |
| 4,235,243 | 11/1980 | Saha . |
| 4,242,911 | 1/1981 | Martin . |
| 4,361,154 | 11/1982 | Pratt . |
| 4,383,533 | 5/1983 | Lovelace et al. . |
| 4,421,119 | 12/1983 | Pratt . |
| 4,446,737 | 5/1984 | Hottier . |
| 4,476,873 | 10/1984 | Sorenson . |
| 4,522,068 | 6/1985 | Smith . |
| 4,530,360 | 7/1985 | Duarte . |
| 4,658,827 | 4/1987 | He et al. . |
| 4,669,482 | 6/1987 | Ophir et al. . |
| 4,688,428 | 8/1987 | Nicolas . |
| 4,702,258 | 10/1987 | Nicolas et al. . |
| 4,774,959 | 10/1988 | Palmer et al. . |
| 4,830,015 | 5/1989 | Okazaki . |
| 4,913,157 | 4/1990 | Pratt et al. . |
| 4,930,511 | 6/1990 | Rossman et al. . |
| 5,042,489 | 8/1991 | Wiener et al. . |
| 5,054,490 | 10/1991 | Rossman et al. . |
| 5,099,849 | 3/1992 | Rossman et al. . |
| 5,119,820 | 6/1992 | Rossman et al. . |
| 5,218,963 | 6/1993 | Mazess . |
| 5,271,403 | 12/1993 | Paulos . |
| 5,343,863 | 9/1994 | Wiener et al. . |
| 5,349,959 | 9/1994 | Wiener et al. . |
| 5,452,722 | 9/1995 | Langton . |
| 5,483,965 | 1/1996 | Wiener et al. . |
| 5,547,459 | 8/1996 | Kaufman et al. . |
| 5,564,423 | 10/1996 | Mele et al. . |
| 5,603,325 | 2/1997 | Mazess et al. . |
| 5,649,538 | 7/1997 | Langton . |
| 5,651,363 | 7/1997 | Kaufman et al. . |
| 5,785,656 | 7/1998 | Chiabrerra et al. ............ 600/449 |
| 5,806,520 | 9/1998 | Berger et al. ................. 600/449 |
| 5,810,732 | 9/1998 | Hamatsu et al. . |

FOREIGN PATENT DOCUMENTS

WO 80/02796  6/1980  WIPO .

OTHER PUBLICATIONS

Agren, M., et al., Calc Tiss Int, vol. 48, pp. 240–244, 1991.
Biot, M. A., J Acoust Soc Am, vol. 34, pp. 1254–1264, 1962.
Blake, G. M., et al., Br J Radiol, vol. 67, pp. 1206–1209, 1994.
Brooke–Wavell, K., et al., Calc Tissue Int, vol. 57, pp. 20–24, 1995.
Chappard, C., et al., Osteoporosis Int, vol. 7, pp. 316–322, 1997.

(List continued on next page.)

*Primary Examiner*—Francis J. Jaworski

[57] ABSTRACT

The invention provides for ultrasonic methods and devices that provide for reproducible positioning of an ultrasonic transducer(s) in the heel using anatomic landmarks for broadband ultrasonic attenuation or speed of sound measurements. The invention provides for improved interrogation devices that reproducibly position transducer(s) over an interrogation site in the heel.

26 Claims, 10 Drawing Sheets

OTHER PUBLICATIONS

Dretakis, E., et al., Br J Radiol, vol. 67, pp. 636–638, 1994.

Evans, W.D., et al., Phys Med Biol, vol. 40, pp. 137–151, 1995.

Faulkner, K. G., et al., Am J Roentgenol, vol. 157, pp. 1229–37, 1991.

Fournier, B., et al., Osteoporosis Int., vol. 7, pp. 363–369, 1997.

Gluer, C. C., et al., J Bone Min Res, vol. 7 (9), pp. 1071–1079, 1992.

Gluer, C. C., et al., Calc Tiss Int, vol. 55, pp. 46–52, 1994.

Goss, S. A., et al., J Acoust Soc Am, vol. 64 (2), pp. 423–457, 1978.

Greenspan, M., et al., J Acoust Soc Am, vol. 31, pp. 75–76, 1959.

Hans, D., et al., Bone, vol. 16, pp. 295–300, 1995.

Johansen, A., et al., Osteoporosis International, vol. 7, pp. 44–47, 1997.

Jorgensen, H. L., et al., Bone, vol. 21, pp. 109–112, 1997.

Kotzki, P. O., et al., Calc Tiss Int, vol. 54, pp. 91–95, 1994.

Lang, P., et al., Radiol Clin North Am, vol. 29, pp. 49–76, 1991.

Langton, C. M., et al., Bone, vol. 18, 6, pp. 495–503, 1996.

Langton, C. M., et al., Eng Med, vol. 13, pp. 89–91, 1984.

Laugier, P., et al., Bone, vol. 20 (2), pp. 157–165, 1997.

Laugier, P., et al., Calc Tiss Int, vol. 58, pp. 326–331, 1996.

Laugier, P., et al., Clinical Rheumatology, vol. 13 (Suppl. 1), pp. 22–32, 1994.

Laugier, P., et al., Calc Tiss Int, vol. 54, pp. 83–86, 1994.

McCloskey, E. V., et al., Clin Sci, vol. 78, pp. 221–227, 1990.

Njeh, C. F., et al., Med Eng Phys, vol. 18, pp. 373–381, 1996.

Roux, C., et al., J Bone Min Res, vol. 11(8), pp. 1112–1118, 1996.

Turner, C. H., et al., Calc Tiss Int, vol. 49, pp. 116–119, 1991.

Williams, J. L., J Acoust Soc Am, vol. 91, pp. 1106–1112, 1992.

Zagzebski, J. A., et al., Calc Tiss Int, vol. 49, pp. 107–111, 1991.

METHODS AND DEVICE FOR IMPROVING BROADBAND ULTRASONIC ATTENUATION AND SPEED OF SOUND MEASUREMENTS USING ANATOMICAL LANDMARKS

TECHNICAL FIELD

The invention relates to ultrasonic methods and devices that provide for reproducible positioning of the ultrasonic transducer(s) over a heel using anatomical landmarks for broadband ultrasonic attenuation and speed of sound measurements.

BACKGROUND

Ultrasonic techniques have recently been introduced as methods free of ionizing radiation for non-invasive assessment of skeletal status in patients with osteoporosis. Quantitative aspects of these ultrasonic techniques can permit assessment of bone mass and density, as well as bone structure. Ultrasonic techniques for evaluating skeletal status also include measurements of speed of sound ("SOS") that reflect the transmission velocity of ultrasonic waves passing through bone tissue and soft tissue and measurements of broadband ultrasonic attenuation ("BUA") that assess the frequency dependence of ultrasonic attenuation.

Many different measurement sites have been proposed for osteoporosis, such as the tibia, the patella, the phalanges, or the calcaneus. The calcaneus is preferred for quantitative ultrasonic measurements of skeletal status. It is composed of predominantly trabecular bone with only a thin cortical bone envelope medially and laterally, which together provide an excellent medium for detecting changes in SOS and BUA measurements. The calcaneus also permits convenient ultrasonic interrogation for the operator and the patient alike.

Although a number of commercial devices exist for diagnosis of osteoporosis, clinicians have recognized the limitations of such devices and methods. Correlations between quantitative ultrasonic measurements and assessments of bone mineral density using quantitative computed tomography, dual x-ray absorptiometry, and single photon absorptiometry have been reported to be poor at the calcaneus, as well as at other sites.

Consequently, the inventors have recognized the need, among other things, to provide reliable ultrasonic devices and accurate, and qualitative or quantitative methods for ultrasonic measurements in the diagnosis of osteoporosis. The methods and devices provided herein permit, among other things, more reproducible speed of sound and broadband ultrasonic attenuation measurements.

SUMMARY

The present invention recognizes for the first time that errors arising from misplacement of interrogation sites in ultrasonic measurements of speed of sound and broadband ultrasonic attenuation of the ankle bone can be corrected by positoning the transducer(s) with respect to an anatomical landmark. Previously, it was not recognized that BUA or SOS measurements could be improved by compensating for positioning errors introduced by soft tissues, growth of the ankle, or interindividual size differences. Nor was it recognized that changes in ankle shape or position are a potential source of decreased accuracy and reproducibility of SOS and BUA measurements in patients with peripheral edema undergoing diuretic or other types of medical treatment of edema with resultant fluctuations in soft tissue thickness. The present invention includes positioning the ankle using A-scan or B-scan technology to identify anatomical locations used for measuring SOS and BUA.

The invention provides for an improved ultrasonic system for tissue BUA or SOS interrogation of a heel, comprising: a) a first ultrasonic transducer with an axis of transmission in common with a second ultrasonic transducer, wherein the axis of transmission is through a portion of tissue of a heel, b) an x, y positioner that engages a first ultrasonic transducer and a second ultrasonic transducer, the x, y positioner controllably positions the first ultrasonic transducer and the second ultrasonic transducer in a desired manner between at least a first and a second position while generally maintaining the axis of transmission, and c) a computational unit designed to manage ultrasonic signal transmission and reception of the first ultrasonic transducer and the second ultrasonic transducer. Typically, the computational unit generates an anatomical landmark from either an A-scan or B-scan in order to direct BUA and SOS measurements. The ultrasonic system may also include a computational unit that can identify an anatomical landmark in the heel and direct the x, y positioner to a position over the anatomic landmark, and thereby positioning the first ultrasonic transducer and second ultrasonic transducer to have an axis of transmission generally through the anatomical landmark in the heel.

In another embodiment, the invention includes an ultrasonic system for automated ultrasonic identification of an anatomical landmark in the heel, comprising: a) an ultrasonic transducer unit comprising a pair of ultrasonic transducers where a first member of the pair is designed to transmit signals and a second member of the pair is designed to receive signals, and b) a computational unit designed to manage ultrasonic signal transmission and reception of the ultrasonic transducer unit for BUA and SOS measurements in the heel and to process signals to identify an anatomical landmark in the heel in either a A scan or B-scan mode or both. The ultrasonic system can further comprise a positioning unit for changing the spatial relationship between the anatomic landmark in the anatomical region and the ultrasonic transducer unit, thereby permitting interrogation with reference to the anatomical landmark in the heel by positioning the transducer unit with respect to the anatomical landmark.

In another embodiment, the invention includes an ultrasonic method for generating an anatomic landmark for ultrasonic interrogation of a heel, comprising: positioning, with respect to an anatomical region of a heel, an ultrasonic transducer unit comprising a pair of ultrasonic transducers where a first member of the pair is designed to transmit signals and a second member of the pair is designed to receive signals, interrogating the anatomical region with the ultrasonic transducer unit, identifying an anatomical landmark in the anatomical region with an ultrasonic property of the heel, and storing the anatomic landmark in a storage device. The ultrasonic method may include the steps of comparing the location of the ultrasonic transducer unit to the location of the anatomical landmark in the heel and positioning the ultrasonic transducer unit at a preselected or desired set of coordinates in relation to the anatomical landmark of the heel.

In another embodiment, the invention includes a computer program product, comprising:
 a) instructions for a positioning unit to position a transducer unit at a plurality of interrogation sites in an anatomical region of a heel,
 b) instructions for interrogating said anatomical region with said transducer unit at said plurality of interrogation sites, c) instructions for generating a map of said anatomical region using ultrasonic measurements from said plurality of interrogation sites,
d) instructions for said positioning unit to position said transducer or said plurality of transducers at a second plurality of interrogation sites in said anatomical region if said map lacks sufficient features to be clinically relevant for a clinically relevant BUA or SOS measurement,
e) instructions for interrogating said anatomical region of the heel for a clinically relevant BUA and SOS measurement;

wherein instructions (a) through (e) permit the generation of the map which facilitates a clinically relevant BUA or SOS measurement and instructions (a) through (e) are stored on a computer retrievable medium. The computer program product can also include instructions for comparing the map with a reference map of substantially the same anatomical region using predefined criteria, the predefined criteria optionally comprising percent similarity of contours of bones, percent similarity of an anatomical landmark or percent similarity of reflective surfaces of the heel; instructions for interrogating the anatomical region for a clinically relevant BUA or SOS measurement if the map matches the reference map; and instructions for the positioning unit to position the transducer unit at a second plurality of interrogation sites in the anatomical region if the map lacks sufficient features to be clinically relevant for a clinically relevant BUA or SOS measurement.

DETAILED DESCRIPTION OF THE INVENTION

1.0 ABBREVIATIONS AND DEFINITIONS

Figure 1:
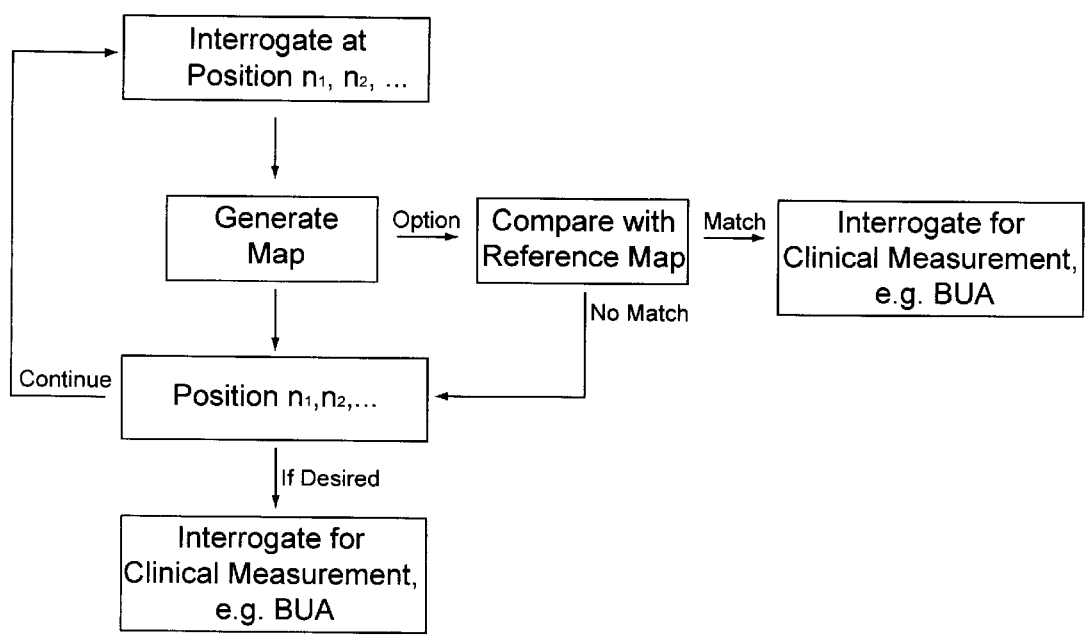
FIG. 1 shows one embodiment of the invention relating to methods of interrogating a heel, generating an anatomical map or instructing a positioner to position a transducer(s) for BUA or SOS measurements. An anatomical map is generated from data by interrogating the tissue at a first transducer (s) position(s) ($n_1$), for instance using either A scan or B-scan or both. A BUA or SOS measurement is then made at the first position $n_1$. The process of interrogation, map generation and clinical measurement can be repeated at each subsequent position ($n_1, n_2, \ldots$). Optionally, the anatomical map can be compared to a reference map that is usually stored in computational unit. When a suitable match occurs with the reference map, BUA or SOS measurement can be initiated.

ABBREVIATIONS include broadband ultrasonic attenuation (BUA) and speed of sound (SOS).

Acoustic communication refers to the passage of ultrasonic waves between two points in a predetermined manner. Usually, this is accomplished by selecting a desired pathway between the two points that permits the passage of ultrasonic waves either directly or indirectly. Direct passage of ultrasonic waves would occur, for instance, when an ultrasonic crystal is directly disposed to (usually touching) an acoustic coupling material, such as a composite. Indirect passage of ultrasonic waves would occur, for instance, when an ultrasonic crystal is located at a predetermined distance from an acoustic coupling material or when a number of acoustic coupling materials, often heterogenous materials, form two or more layers.

Anatomical region refers to a site on the surface of the skin, tumor, organ or other definable biomass that can be identified by an anatomical feature(s) or location. Anatomical region can include the biomass underlying the surface. Usually, such a region will be definable according to standard medical reference methodology, such as that found in Williams et al., Gray's Anatomy, 1980.

BUA means broadband ultrasonic attenuation and when measured a BUA value is expressed as dB/MHz. Note that actual attenuation of broadband ultrasonic waves increases as soft tissue thickness increases, while BUA values (dB/MHz) decrease as soft tissue thickness increases. This distinction is often not recognized in the literature, which leads to misleading or potentially misleading conclusions about the effect of soft tissue on actual attenuation of broadband ultrasonic waves and BUA values.

A-scan refers to an ultrasonic technique where an ultrasonic source transmits an ultrasonic wave into an object, such as a patient's body, and the amplitude of the returning echoes (signals) are recorded as a function of time. Structures that lie along the direction of propagation are interrogated. As echoes return from interfaces within the object or tissue, the transducer crystal produces a voltage that is proportional to the echo intensity. The sequence of signal acquisition and processing of A-scan data in a modern ultrasonic instrument usually occurs in six major steps:

Detection of the echo (signal) occurs via mechanical deformation of the piezoelectric crystal and is converted to an electric signal having a small voltage.

Preamplification of the electronic signal from the crystal, into a more useful range of voltages is usually necessary to ensure appropriate signal processing.

Time Gain Compensation compensates for the attenuation of the ultrasonic signal with time, which arises from travel distance. Time gain compensation may be user-adjustable and may be changed to meet the needs of the specific application. Usually, the ideal time gain compensation curve corrects the signal for the depth of the reflective boundary. Time gain compensation works by increasing the amplification factor of the signal as a function of time after the ultrasonic pulse has been emitted. Thus, reflective boundaries having equal abilities to reflect ultrasonic waves will have equal ultrasonic signals, regardless of the depth of the boundary.

Compression of the time compensated signal can be accomplished using logarithmic amplification to reduce the large dynamic range (range of smallest to largest signals) of the echo amplitudes. Small signals are made larger and large signals are made smaller. This step provides a convenient scale for display of the amplitude variations on the limited gray scale range of a monitor.

Rectification, demodulation and envelope detection of the high frequency electronic signal permits the sampling and digitization of the echo amplitude free of variations induced by the sinusoidal nature of the waveform.

Rejection level adjustment sets the threshold of signal amplitudes that are permitted to enter a data storage, processing or display system. Rejection of lower signal amplitudes reduces noise levels from scattered ultrasonic signals.

B—scan refers to an ultrasonic technique where the amplitude of the detected returning echo is recorded as a function of the transmission time, the relative location of the detector in the probe and the signal amplitude. This is often represented by the brightness of a visual element, such as a pixel, in a two-dimensional image. The position of the pixel along the y-axis represents the depth, i.e. half the time for the echo to return to the transducer (for one half of the distance traveled). The position along the x-axis represents the location of the returning echoes relative to the long axis of the transducer, i.e. the location of the pixel either in a superoinferior or mediolateral direction or a combination of both. The display of multiple adjacent scan lines creates a composite two-dimensional image that portrays the general contour of internal organs.

Chip refers to any current and future electronic hardware device that can be used in a computational unit and can be used as an aid in controlling the components of an ultrasonic unit including: 1) timing and synchronizing trigger pulses and subsequent transmission of ultrasonic waves, 2) measuring and analyzing incoming ultrasonic signals, 3) comparing data to predetermined standards and data cut-offs (e.g. electronic filtering), and 4) performing multiple other simple and complex calculations. Typically, a chip is silicon-based, micro-electronic ciruit.

Computational unit refers to any current or future hardware, software (e.g. computer program), chip or other device used for calculations or for providing instructions now developed or developed in the future or combination thereof. The computational unit may be used for controlling the ultrasonic generator or source, for defining or varying the firing rate and pulse repetition rate (as well as other parameters related to the ultrasonic generator or source), for measuring a reflected signal, for image reconstruction in B-scan mode and for filtering of the ultrasonic signal. Other applications of the computational unit to the methods and devices described herein will be recognized by those skilled in the art. The computational unit may be used for any other application related to this technology that may be facilitated with use of computer software or hardware. The computational unit may comprise a computer program product with instructions to control the ultrasonic system. Such computer program products may be stored in storage devices, such as hard drives, floppy discs, eletronic storage devices or any other storage device capable of reliable storage and retrieval of information (including electronic signals).

Detector refers to any structure capable of measuring an ultrasonic wave or pulse, currently known or developed in the future. Crystals containing dipoles are typically used to measure ultrasonic waves. Crystals, such as piezoelectric crystals, shift in dipole orientation in response to an applied electric current. If the applied electric current fluctuates, the crystals vibrate to cause an ultrasonic wave in a medium.

Conversely, crystals vibrate in response to an ultrasonic wave that mechanically deforms the crystals, which changes dipole alignment within the crystal. This, in turn, changes the charge distribution to generate an electric current across a crystal's surface. Electrodes connected to electronic circuitry sense a potential difference across the crystal in relation to the incident mechanical pressure. A transducer can be a detector.

Echogenicity refers to the brightness of a tissue in an ultrasonic image relative to the adjacent tissues, typically on a B-scan image. Echogenicity is dependent on the amount of ultrasonic waves reflected by the tissue. Certain tissues are more echogenic than other tissues. Fatty tissue, for example, is more echogenic than muscle tissue. For identical imaging parameters, fatty tissue will thus appear brighter than muscle tissue. Consequently, image brightness can be used to identify different tissues.

Linear array refers to a transducer design where the crystals are arranged in a linear fashion along one or more axes. Crystals can be fired in sequential, as well as non-sequential and simultaneous firing patterns or a combination thereof. With sequential firing, each crystal can produce an ultrasonic beam and receive a returning echo for data collection. The number of crystals in one array usually determines the number of lines of sight for each recording. With segmental firing, a group or segment of crystals can be activated simultaneously resulting in a deeper near field and a less divergent far field compared with sequential activation. A segmental linear array produces, however, a smaller number of lines of sight when compared to a sequential linear array with the same number of crystals.

Osteoporosis refers to a condition characterized by low bone mass and microarchitectural deterioration of bone tissue, with a consequent increase of bone fragility and susceptibility to fracture. Osteoporosis presents most commonly with vertebral fractures due to the decrease in bone mineral density and deterioration of structural properties of the bone. The most severe complication is hip fracture due to its high morbidity and mortality.

Plane refers to the surface of a cross-sectional area of tissue interrogated by an ultrasonic probe. In ultrasonic measurements, the portion of the tissue included in the measurement or image is more accurately referred to as a volume. The x-dimension of this volume reflects the length of the tissue plane, i.e. the length of imaged tissue. The x-dimension typically varies between 1 and 10 cm or more. The y-dimension of this volume reflects tissue depth from the plane, e.g. the distance from the skin surface to a reflection point in the tissue. Interrogation of the y-dimension (or depth of the interrogation) depends, among other things, on the type of transducer, the type of tissue, and the frequency with which the ultrasonic beam is transmitted. With higher frequencies, tissue penetration decreases and the maximum depth from the tissue plane will decrease. The y-dimension typically varies between 1 and 30 cm. The z-dimension corresponds to the width of the plane that is interrogated. It typically varies between 1 and 15–20 mm. It is understood that such dimensions are in reference to ultrasonic signals and interrogation. In addition, x, y, and z dimensions are also used with different meaning in the context of positioning probes, and devices for locating probes in different areas of an anatomical region.

First position refers to a position of an ultrasonic source (or transducer) that detects or transmits an ultrasonic signal or pulse, respectively.

Second position refers to a position of an ultrasonic source (or transducer) that transmits or detects an ultrasonic pulse or signal, respectively, and having a different anatomical location than the first position. Additional positions can be readily achieved by relocating the ultrasonic source to vary the anatomical location of interrogation.

Transmission frequency refers to the frequency of the ultrasonic wave that is being transmitted from the ultrasonic source. Transmission frequency typically ranges between 0.2 MHz and 25 MHz. Higher frequencies usually provide higher spatial resolution. Tissue penetration decreases with higher frequencies. Lower transmission frequencies are generally characterized by lower spatial resolution with improved tissue penetration. Frequencies for BIJA measurements typically range from 0.2 MHz to 2 MHz.

Ultrasonic pulse refers to any ultrasonic wave transmitted by an ultrasonic source. Typically, the pulse will have a predetermined amplitude, frequency, and wave shape. Ultrasonic pulses may range in frequency between 20 kHz and 20 Mhz or higher.

Ultrasonic signal refers to any ultrasonic wave measured by an ultrasonic detector after it has been reflected from the interface of an object or tissue. Ultrasonic signals may range in frequency between 20 kHz and 20 Mhz or higher.

Ultrasonic source refers to any structure capable of generating an ultrasonic wave or pulse, currently known or developed in the future. Crystals containing dipoles are typically used to generate an ultrasonic wave above 20 khz. Crystals, such as piezoelectric crystals, that vibrate in response to an electric current applied to the crystal can be used as an ultrasonic source. In some ultrasonic generators, multiple ultrasonic sources may be arranged in a linear fashion. This arrangement of ultrasonic sources is also referred to as a linear array. With linear arrays, ultrasonic sources are typically fired sequentially, although simultaneous firing of groups of adjacent ultrasonic sources or other firing patterns of individual or groups of ultrasonic sources with various time delays can be achieved as described herein or developed in the art. The time delay between individual or group firings can be used to vary the depth of the beam in an object.

Ultrasonic wave refers to either an ultrasonic signal or pulse.

2.0 INTRODUCTION

The present invention recognizes for the first time that errors arising from misplacement of interrogation sites in ultrasonic measurements of speed of sound and broadband ultrasonic attenuation of the ankle bone can be corrected by positoning the transducer(s) with respect to an anatomical landmark. Previously, it was not recognized that BUA or SOS measurements could be improved by compensating for positioning errors introduced by soft tissues, growth of the ankle, or interindividual size differences. Nor was it recognized that changes in ankle shape or position are a potential source of decreased accuracy and reproducibility of SOS and BUA measurements in patients with peripheral edema undergoing diuretic or other types of medical treatment of edema with resultant fluctuations in soft tissue thickness. The present invention includes positioning the ankle using A-scan or B-scan technology to identify anatomical locations used for measuring SOS and BUA.

Without limiting aspects of the invention to a particular mechanism of action, the inventors believe that the poor correlations between quantitative ultrasonic techniques and other methods for assessing bone mineral density are often caused by variations in the position of the interrogated bone with respect to the ultrasonic transducers. Sources of such interrogation artifacts include variations in the thickness of the posterior or inferior heel pads that can, in turn, change the position of the calcaneus relative to the ultrasonic transducers. In all cases, differences in the amount and region of bone interposed in the ultrasonic beam path can ultimately change and alter the speed of sound or broadband ultrasonic attenuation.

Previous work failed to recognize that soft tissue swelling or fluctuations in soft tissue thickness in patients with peripheral edema can affect ultrasonic probe position relative to the underlying bone or other underlying structures in the heel. The inventors were the first to recognize that changes in ultrasonic probe position relative to the underlying bone induced by local or generalized soft tissue swelling or fluctuations in soft tissue thickness can reduce short-term and long-term in vivo precision of SOS and BUA measurements. The inventors were also the first to recognize that soft tissue swelling induced changes in ultrasonic probe position relative to the underlying bone can be particularly significant in patients with edema undergoing diuretic or other types of medical treatment of edema with resultant fluctuations in soft tissue thickness.

It was also not previously recognized that changes in soft tissue thickness or local heterogeneity in soft tissue thickness may affect ultrasonic probe position relative to the tissue/structure to be measured in BUA and SOS measurements. The present invention overcomes these limitations by providing devices and methods to correct for changes in tissue structure in BUA and SOS measurements. The invention also includes methods and devices based on the identification of anatomic landmarks of the heel to be measured and optionally subsequently positioning of the ultrasonic probes relative to these anatomic landmarks to improve BUA and SOS measurements. The present invention includes also positioning of ultrasonic probes using landmarks based on textural information (e.g. density, SOS, BUA, or a combination thereof) of the ankle. Preferably, many of the embodiments described herein are designed for automated use with a minimum of operator intervention and preferably with remote or computer control of such devices.

By way of introduction, and not limitation of the various embodiments of the invention, the invention includes at least three general aspects:

1) an ultrasonic method of positioning the heel for measurements of speed of sound and broadband ultrasonic attenuation based on anatomical landmarks;

2) an ultrasonic method of BUA or SOS measurement that includes identification of anatomic landmarks of the structure to be measured and subsequently positions the ultrasonic probes over the measurement area using these anatomic landmarks;

3) devices and systems to achieve or facilitate the methods 1 and 2.

These aspects of the invention, as well as others described herein, can be achieved using the methods and devices described herein. To gain a full appreciation of the scope of the invention, it will be further recognized that various aspects of the invention can be combined to make desirable embodiments of the invention. For example, aspects 1 and 2 of the invention can be combined to improve the reproducibility of measurements of SOS and BUA even further.

3.0 AUTOMATED SYSTEM FOR POSITIONING ULTRASONIC TRANSDUCERS AND RELATED METHODS

Ultrasonic Systems and Landmark Detection Systems

The present invention includes an ultrasonic system for ultrasonic interrogation of heel tissue for BUA or SOS. The system is based, in part, on improving BUA or SOS measurements by creating a anatomical landmark, anatomical maps ("maps") or both. In the preferred embodiments the ultrasonic system is adapted to provide anatomical landmarks and interrogate tissues for either broadband ultrasonic attenuation or speed of sound measurements.

The invention also includes an ultrasonic system for tissue BUA or SOS measurements using anatomic landmarks that can be identified by the system. Such a system can include an ultrasonic transducer unit for BUA, SOS, or both comprising a pair of ultrasonic transducers where a first member of the pair is designed to transmit signals and a second member of the pair is designed to receive signals. A computational unit can be part of the system and is designed to manage ultrasonic signal transmission and reception of the ultrasonic transducer unit and to process signals to identify an anatomical landmark in an anatomical region, as well as BUA and SOS measurements. For instance, the computational unit is designed to process ultrasonic signals received from the ultrasonic transducer unit to generate an anatomical map of the anatomical region and identify the anatomic landmark within the anatomical region. The map can provide computer stored coordinates to locate the anatomic landmark within the anatomical region or map for current or future aid in positioning the transducer with x,y positioners, as described herein or known in the art. Typically, anatomical landmarks are about 10 percent or less of the area of a map and preferably less than about 2 to 0.2 cm. Preferably, the transducer units and computational unit have adapted A-scan or B-scan operation and more preferably can be used for measuring other ultrasonic properties as described herein or have transducers adapted to measure such other properties. Preferably, the process of identifying an anatomical landmark is programmed into the computational unit to permit highly automated interrogation. Such an anatomical landmark can either allow an operator to locate a transducer or allow a computer to locate a transducer or some combination thereof.

In many embodiments of a landmark system it will be useful to compare landmarks within an anatomical region for BUA or SOS measurement. The same landmark may be compared at different times (intra-landmark comparison) or one or more landmarks may be compared (inter-landmark comparison). For instance, an intra-landmark comparison can be used during a single interrogation protocol that entails multiple interrogations of the same region with reference to a particular anatomical landmark. The computational unit can also further comprise a database comprising reference anatomical maps and the computational unit is further designed to compare the anatomical map with the reference anatomical map. The reference anatomical map may be historic (from the same or another patient, generated as part of an interrogation protocol), or theoretical or any other type of desired reference map. The reference map can include a reference anatomical landmark, or if desired the landmark may be stored alone.

Automated Positioning System

The present invention includes an ultrasonic system for ultrasonic interrogation of tissue using BUA or SOS. The system is based, in part, on improving ultrasonic measurements by creating a desired spatial relationship between two ultrasonic transducers and their transmission paths (or reception paths) in the heel based on an anatomical landmark. In the preferred embodiments, the ultrasonic system is adapted to automatically interrogate dense tissues of the heel to measure either broadband ultrasonic attenuation or speed of sound.

Typically, such a system includes a first ultrasonic transducer with an axis of transmission in common with a second ultrasonic transducer. The axis of transmission is usually through a portion of a dense tissue and usually the transducers are not permanently fixed but are capable of being repositioned to a predetermined or desired location. The two transducers can be aligned (e.g. mechanically aligned) to have a common axis of transmission. In such situations, the transducers will be generally directed at each other to receive signals from each other. The transducers may not have an axis of transmission in common but are instead arranged to each have a predetermined axis of transmission, wherein each transducer may send signals that can be received by the other transducer without having a common axis of transmission. Preferably, a transducer is included that is adapted for A-scan or B-scan mode and can be used for anatomical landmarks and maps as discussed herein. Alternatively, tandem transducers can be used wherein each tandem transducer is comprised of 1) a transducer designed for A-scan or B-scan, and 2) a transducer designed for either broadband ultrasonic attenuation or speed of sound measurements or both. It is understood that a tandem transducer can be paired so that, for instance, the broadband ultrasonic transducer in the first tandem transducer transmits signals and the broadband ultrasonic transducer in the second tandem transducer receives signals.

Typically, the site of interrogation of each transducer is at least about 1 cm apart, often at least about 4 cm apart and sometimes about 6 cm or more cm apart. Transducers at interrogation sites can also be positioned on different faces or sides of a heel to be interrogated (e.g. on the medial and lateral portion of the heel). In many of these embodiments the transducers receive signals from each other. Preferably, tandem transducers are used that are adapted or programmed to receive signals from each other.

Generally, the system will include an x, y positioner that engages the first ultrasonic transducer and the second ultrasonic transducer to position each transducer in the appropriate position on the heel for BUA or SOS. Usually, the x, y positioner positions the first ultrasonic transducer and the second ultrasonic transducer while generally maintaining the axis of transmission. The x,y positioner can be designed to include positioning of each transducer independently or positioning of each transducer while simultaneously maintaining a common axis of transmission. The x, y positioner can position the ultrasonic transducer at a desired location along the x axis and y axis of the system. Typically, the x axis is the horizontal axis and the y axis is vertical axis. Preferably, a z-positioner will be included in the positioning unit to move a transducer to or away from an interrogation site.

A computational unit can be included in the system to manage ultrasonic measurements. Typically, the computational unit is designed to manage ultrasonic signal transmission and reception of the first ultrasonic transducer and the second ultrasonic transducer. It may also be designed to optionally control movement of the positioning unit (e.g. x, y positioner). By monitoring signal transmission and reception the computational unit can instruct the x, y positioner to appropriately locate the transducers in order to achieve the desired relationship between the position of each transducer and the heel. For example, FIG. 1 shows one method of instructing a positioner and interrogating a tissue for BUA or SOS based on anatomical maps. In many instances the computational unit can be programmed to instruct the x, y positioner to establish a common axis of transmission between the two transducers. As described herein, this is a particularly useful embodiment for broadband ultrasonic attenuation and speed of sound measurements in the human heel.

In greater detail, FIG. 1 shows one embodiment of the invention relating to methods of interrogating a tissue for BUA or SOS, generating an anatomical map and instructing a positioner to position a transducer(s). An anatomical map is generated from data obtained by interrogating the tissue at a first transducer(s) position(s) ($n_1$). This can be done using any ultrasonic measurement, such as A-scan or B-scan or both. The BUA or SOS measurement is then made at the first position $n_I$. The process of interrogation, map generation and BUA or SOS measurement can be repeated at each subsequent position ($n_1$ $n_2$, . . . ). Optionally, the anatomical map can be compared to a reference map that is usually stored in the computational unit. When a suitable match occurs with the reference map, interrogation can be initiated for BUA or SOS. Such matches can be based on predetermined match criteria, including anyone or combination of the following criteria: percentage of contour overlap, homology between ultrasonic features in a given map (such as the percentage of features in common), and the proximity of a set of coordinates in the anatomical map to a defined set of coordinates in the reference map. If no match occurs, the positioner repositions the transducer(s), another interrogation occurs and another map is generated and compared to the reference map. This process can be repeated until the desired match is obtained or until it is determined that no suitable match is possible. Typically, the positioner moves the transducer in increments until the desired location or interrogation site has been reached and the tissue is interrogated for BUA or SOS measurement. Such methods can be adapted as instructions for components of a monitoring system that form a computer program product.

A system for BUA or SOS measurements that includes two, or more ultrasonic transducers, a positioning unit (e.g. an x, y positioner), and a computational unit for signal management and transducer positioning offers a number of advantages. First, transducer positioning can be automatically established without significant operator intervention, as well as with operator direction to a desired position. Second, accuracy and reproducibility of transducer positioning can be improved by appropriately programming the computational unit. Finally, adjustments to transducer positioning during interrogation can be accomplished with minimized interruption of the interrogation process.

In another embodiment the computational unit directs a positioning unit to position the transducer unit with reference to the anatomical landmark prior to BUA or SOS measurement. Preferably, anatomical landmarks in the heel are less than about 2 $cm^2$, more preferably about less than 1 $cm^2$, and most preferably less than about 0.5 $cm^2$, unless the anatomical landmarks are based on contours. The transducer can be positioned by an iterative process to find a preprogrammed landmark (e.g. historic) or to identify a landmark by preprogrammed criteria. Typically, the computational unit is designed to instruct the transducer unit to transmit and receive signals after positioning the transducer unit with respect to the anatomical landmark. This process can be repeated and is outlined in FIG. 2.

Figure 2:
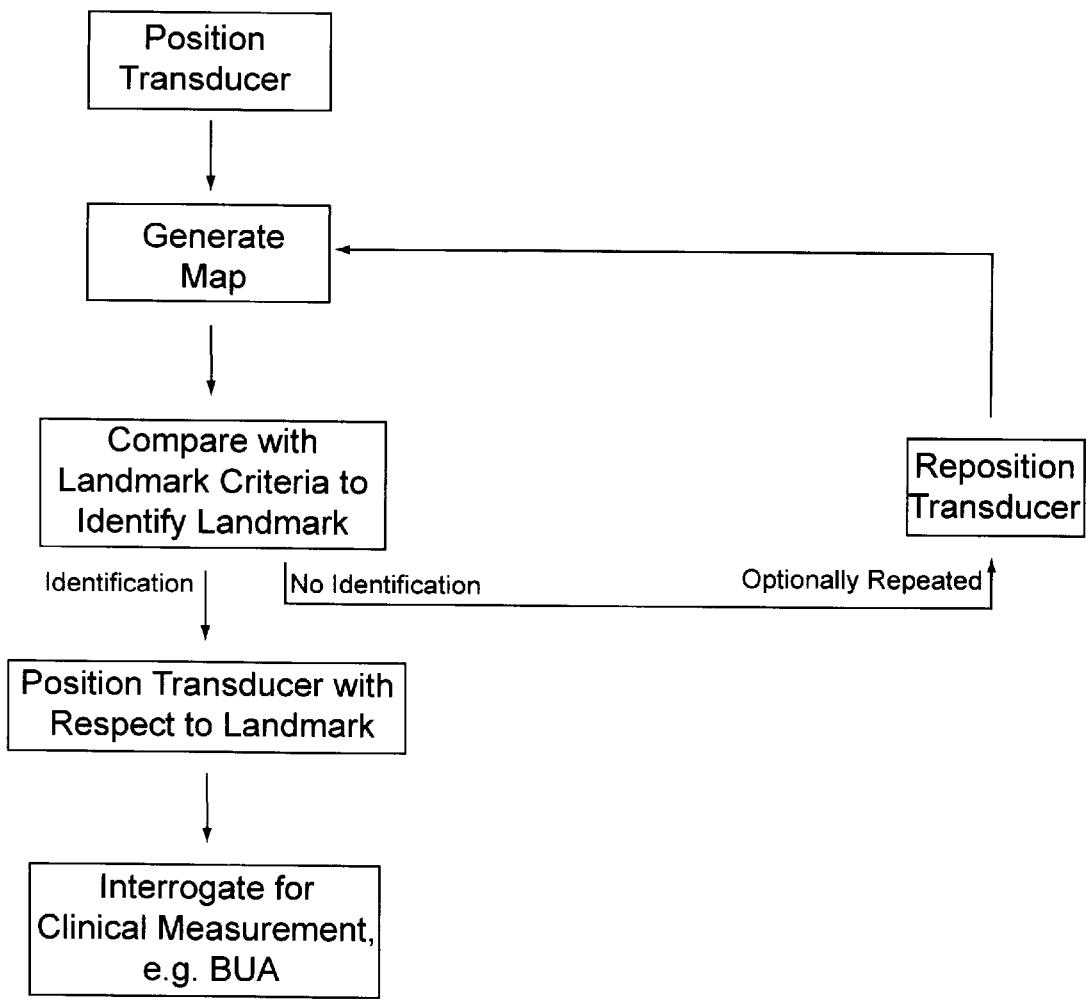
FIG. 2 shows another embodiment of the invention relating to methods of interrogating a heel, identifying an anatomical landmark or instructing a positioner to position a transducer(s). The transducer(s) is positioned. An anatomical map is generated from data by interrogating the tissue at a first transducer(s) position(s) ($n_1$), for instance using either A-scan or B-scan or both. A comparison of the map to landmark criteria is then made to identify a landmark at the first position $n_1$. The process of positioning, interrogation, map generation and comparison can be repeated at each subsequent position ($n_1, n_2, \ldots$). After a landmark has been identified, a BUA or SOS measurement can be initiated.

In greater detail, FIG. 2 shows another embodiment of the invention relating to methods of interrogating a tissue for BUA or SOS, identifying an anatomical landmark and instructing a positioner to position a transducer(s). The transducer(s) is (are) positioned. An anatomical map is generated from data obtained by interrogating the tissue at a first transducer(s) position(s) ($n_1$). This can be done using any ultrasonic measurement, such as A-scan or B-scan or both. A comparison of the map to landmark criteria is then made to identify a landmark at the first position nl. The process of positioning, interrogation, map generation and comparison can be repeated at each subsequent position ($n_1$ $n_2$, . . . ). After a landmark has been identified, a BUA or SOS measurement can be initiated. Typically, a computational unit directs a positioning unit to position the transducer unit with reference to an anatomical landmark. The transducer can be positioned by an iterative process to identify a landmark, e.g. based on preprogrammed landmark criteria. Typically, the computational unit is designed to instruct the transducer unit to transmit and receive signals after positioning the transducer unit with respect to the anatomical landmark. Such methods can be adapted as instructions for components of a monitoring system that form a computer program product.

The ultrasonic system can further comprise a positioning unit for changing the spatial relationship between the anatomic landmark in the heel and the ultrasonic transducer unit, thereby permitting interrogation for BUA or SOS with reference to the anatomic landmark in the anatomical region by positioning the transducer unit with respect to the anatomical landmark. The computational unit can further comprise a display for showing the anatomical map.

The system may optionally include a z positioner that engages and/or positions at least one or more ultrasonic transducers. Preferably, both transducers can be positioned in the z dimension by the z positioner. The z positioner changes the distance of transmission along the axis of transmission between the first ultrasonic transducer and the second ultrasonic transducer. Typically, it changes the distance between the transducer and the interrogation site. The z positioner can position the ultrasonic transducer at a desired location along the z axis of the system. Typically, the z axis is the axis perpendicular to the x axis which is the horizontal axis, and the y axis is the vertical axis. The z positioner moves the transducer(s) along the z-axis further or closer to the surface of the anatomical location.

The x, y positioner included in the system can be any positioner that can accurately position a transducer and maintain the transducer position during interrogation. The x, y positioner can be those known in the art of positioning devices or those developed in the future or disclosed herein. In selecting an x, y positioner the following features should considered and incorporated into the x, y positioner design depending on the application: 1) ease of movement of the positioner preferably with automated control, 2) integration of the positioner into a computer control system, 3) accuracy of positioning (preferably within about ±5 mm, more preferably about ±1 mm and most preferably about ±0.05 mm), 4) speed of achieving a new position should typically be less than 2 to 4 seconds, and 5) ability of the x, y positioner to either locate one transducer or two transducers. It is understood that the x, y positioner may be configured in many arrangements. For instance, the x, y positioner may be designed as one positioning system that moves each transducer concurrently or as two x, y positioners that move each transducer independently yet in a coordinated fashion with respect to each transducer. The x, y positioner can be manually controlled, operator computer controlled, or automatically controlled with minimal or no operator intervention or a combination thereof. Preferably, the system is capable of all three modes of operation. If a manual mode is incorporated into the device, the x, y positioner typically includes a grip to manually direct the first and second transducers over a desired anatomic region. Positioners in the art may used as well, such as those provided by Newport (Irvine, Calif.), including stages for rectilinear motion. The positioning unit can be operated and designed for manual, computer operator or automatic operation. Positioning units can be those devices known in the art or described herein to accomplish such functions.

In one embodiment, the x, y positioner can comprise a frame to maintain the axis of transmission between the first and second ultrasonic transducers. In this embodiment the x, y positioner maintains a "fixed" axis of transmission. Typically, these types of positioners can be less expensive to operate and robust under a variety of clinical conditions because the axis of transmission is fixed, typically during manufacture or in an adjustment protocol. Thus, the x, y positioner is not required to locate the transducer with respect to one another since this is predetermined. Instead the x, y positioner can be primarily designed to locate the transducer in tandem with a fixed common axis of transmission in relation to the anatomic region of interrogation. Typically, the frame engages an x track and the x track engages a y track, thereby an operator can move the first and second ultrasonic transducers manually in either an x or y dimension or combination thereof with respect to an anatomic region. It is understood, however, that such tracks could also be located on separate frames without a fixed common axis of transmission between the two transducers and that a common axis of transmission could be established. The x, y positioner can be designed to accommodate the heel. Typically, the heel is held in a predetermined position in the ultrasonic system relative to the x, y positioner. Preferably, the x, y positioner is automatically controlled by the computational unit. In one arrangement, the computational unit instructs an x servo-motor to drive the first ultrasonic transducer and second transducer in the x dimension and a y servo-motor to drive the first ultrasonic transducer and second transducer in the y dimension.

A key and useful feature of some embodiments of the invention is an ultrasonic system wherein the computational unit comprises a computational program to identify an anatomic landmark in the heel in conjunction with BUA or SOS measurements, as described further herein. For example, the ultrasonic system can be designed wherein the computational unit is designed to instruct the x, y positioner to position the first ultrasonic transducer and the second ultrasonic transducer to identify and interrogate the anatomic landmark in the heel. Usually, the x,y positioner generally maintains the axis of transmission between the first ultrasonic transducer and the second ultrasonic transducer and generally through the anatomic landmark of the heel.

The anatomical landmark that is selected is part of an anatomical region appropriate for BUA or SOS measurements in the heel, such as locations of dense bone. Other anatomical regions can be selected from the group consisting of a knee and tibia. The x, y positioner can be adapted to accommodate the anatomical site. Preferably, at least the first ultrasonic transducer and the second ultrasonic transducer are adapted for either speed of sound or broadband ultrasonic attenuation (or both) measurements in heel tissue comprising bone. In another embodiment the computational unit can identify an anatomic landmark in an interrogated tissue and direct the x, y positioner to position over the anatomic landmark, thereby the first ultrasonic transducer and second ultrasonic transducer have an axis of transmission generally through the anatomic landmark.

As an example of the invention, the use of an x, y positioner either alone or in conjunction with an anatomic landmark can facilitate speed of sound or broadband ultrasonic attenuation measurements in the heel. By including an x, y positioner in an ultrasonic system, the transducers can be positioned to generally maintain an interrogation site that takes into account tissue swelling (or possibly growth). By including a landmark detection system, as described herein, even more reproducible and accurate measurements can be made.

Additional Soft Tissue Correction Devices Current ultrasonic probes for measuring SOS and BUA are hand positioned using visible or palpable regions on the skin surface (e.g. sole of the foot, posterior margin of the heel). In the calcaneus, pathologic soft tissue thickening, e.g. from tissue edema, will change the position of the calcaneus relative to the transducer on the skin surface. Thus, the transducer(s) will measure over the same external area, but will not measure the same area in the calcaneus. This effect can be particularly pronounced if edema/soft tissue thickness changes between follow-up examinations (e.g. baseline examination in am with little or no edema, follow-up examination in pm with more pronounced edema). Thus, changes in probe position relative to the calcaneus or other bone will affect reproducibility of SOS and BUA significantly.

Figure 3:
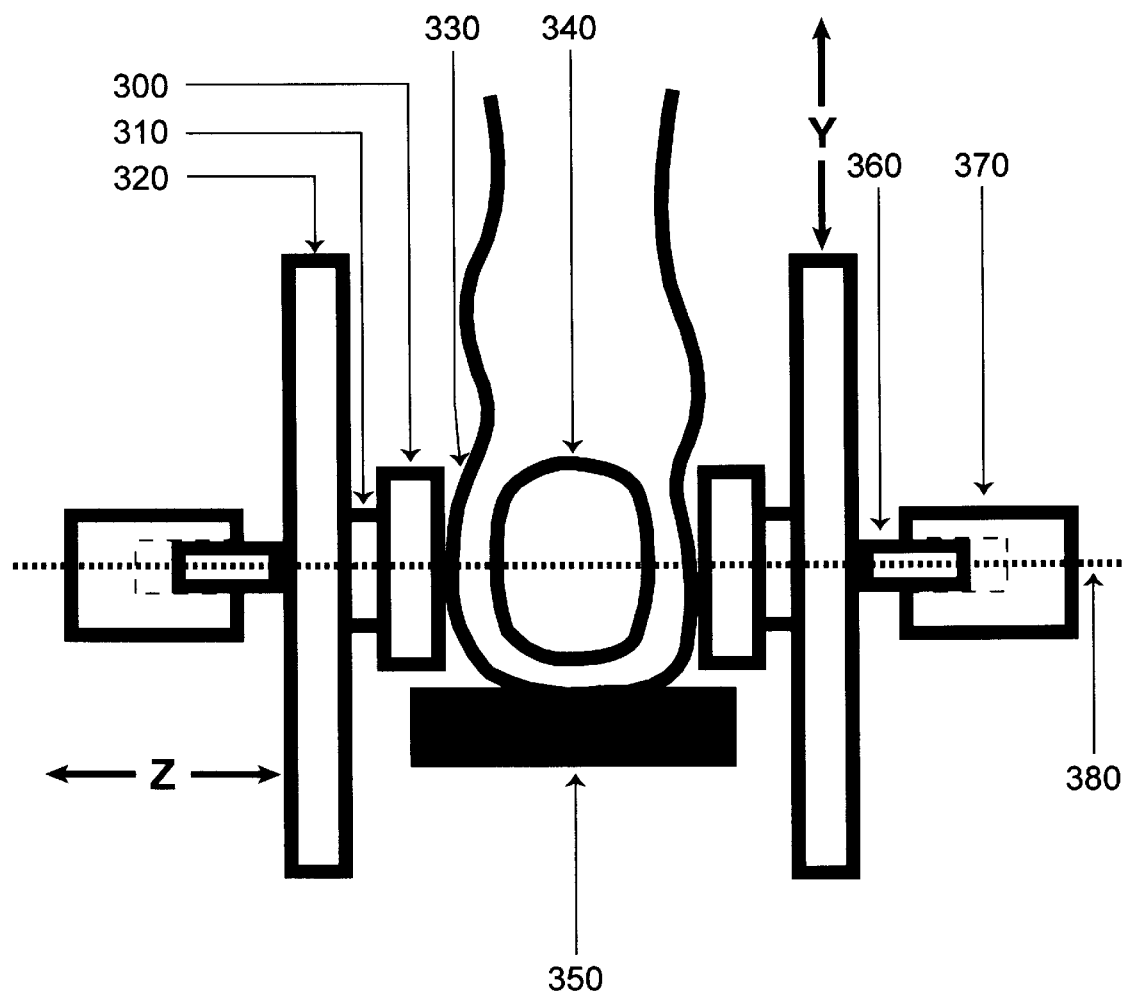
FIG. 3 shows another embodiment of the invention comprising two ultrasonic transducers 300 attached to an x-positioner 310 and a y-positioner 320. The heel 330 and the calcaneus 340 are seated on a foot holder 350. The ultrasonic transducer 300 is brought in contact with the heel 330 using a z-positioner member 360 that can move in and out of a frame 370 continuously or in a stepwise fashion. The ultrasonic transmission axis 380 is also shown.

FIG. 3 shows another embodiment of the invention comprising two ultrasonic transducers 300 attached to an x-positioner 310 and a y-positioner 320. The heel 330 and the calcaneus 340 are seated on a foot holder 350. The ultrasonic transducer 300 is brought in contact with the heel 330 using a z-positioner member 360 that can move in and out of a frame 370 continuously or in a stepwise fashion. The ultrasonic transmission axis 380 is also shown.

Figure 4:
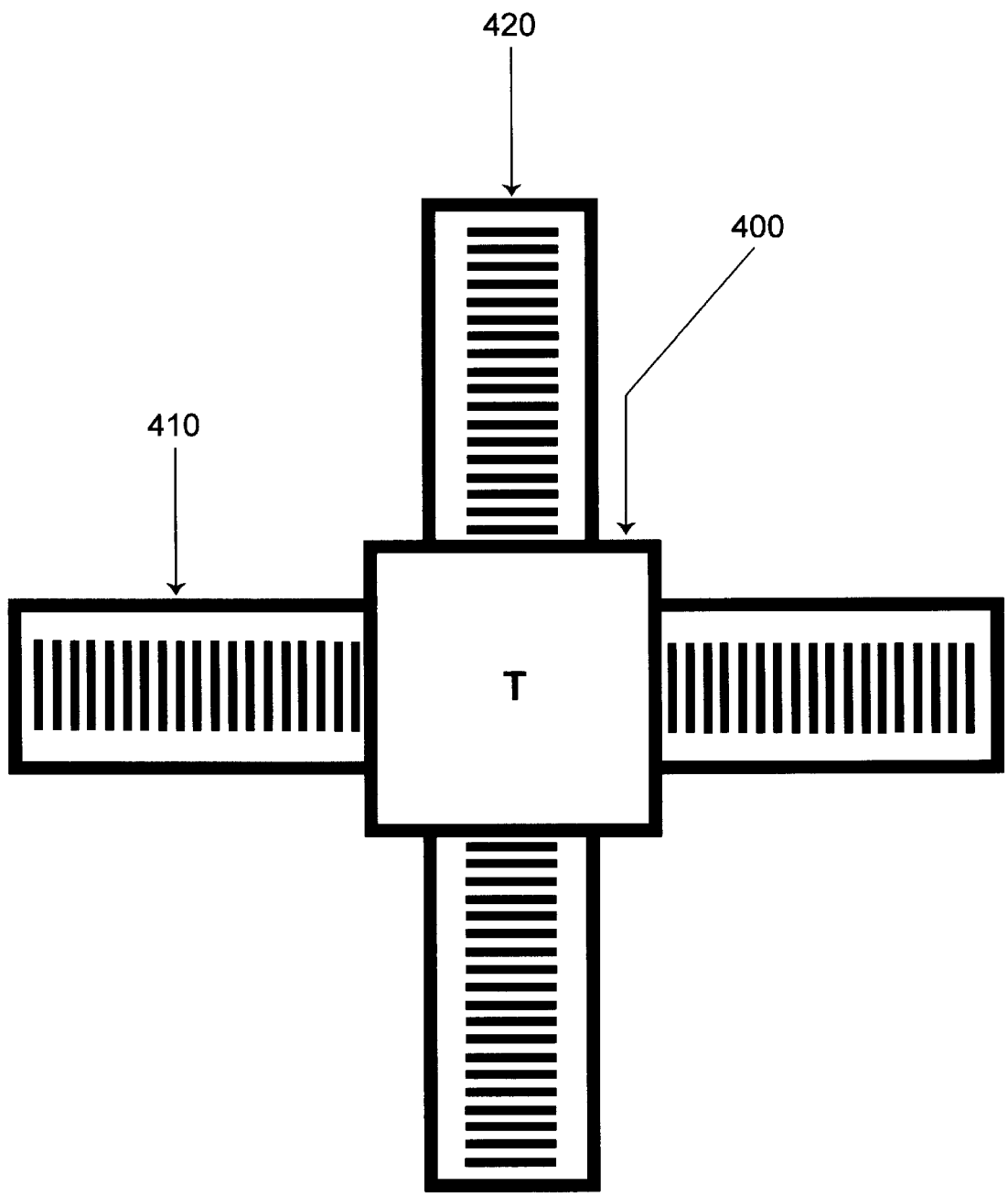
FIG. 4 is a side view of the ultrasonic transducer (T) 400, the x-positioner 410, and the y-positioner 420 shown in FIG. 3 showing the tracks of each positioner. Typically, one positioner will engage the other positioner to permit x, y movement either concurrently (moving in both directions simultaneously) or sequentially (moving in one dimension first and then in a second dimension).

FIG. 4 is a side view of the ultrasonic transducer 400, the x-positioner 410, and the y-positioner 420 shown in FIG. 3 showing the tracks of each postioner. Typically, one positioner will engage the other positioner to permit x, y movement either concurrently (moving in both directions simultaneously) or sequentially (moving in one dimension first and then in a second dimension).

Figure 5A:
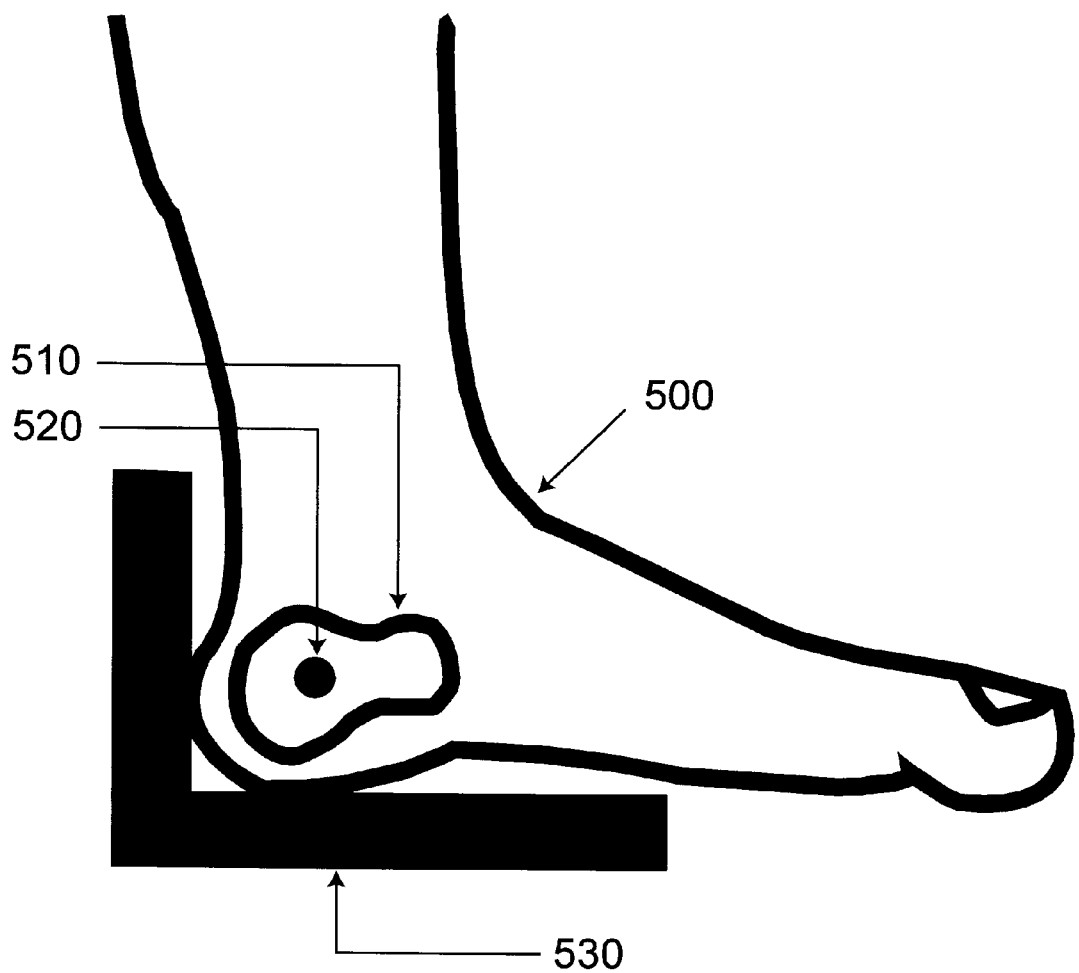
FIG. 5A shows an example of a typical prior art device for measuring the speed of sound or broadband ultrasonic attenuation in a healthy non-edematous patient. The position of the patient's foot 500, of the calcaneus 510, and of the ultrasonic interrogation site 520 are fixed with respect to the device frame 530.

FIG. 5A shows an example of a typical prior art device for measuring the speed of sound or broadband ultrasonic attenuation in a healthy non-edematous patient. The position of the patient's foot 500, of the calcaneus 510, and of the ultrasonic interrogation site 520 are fixed with respect to the device frame 530.

Figure 5B:
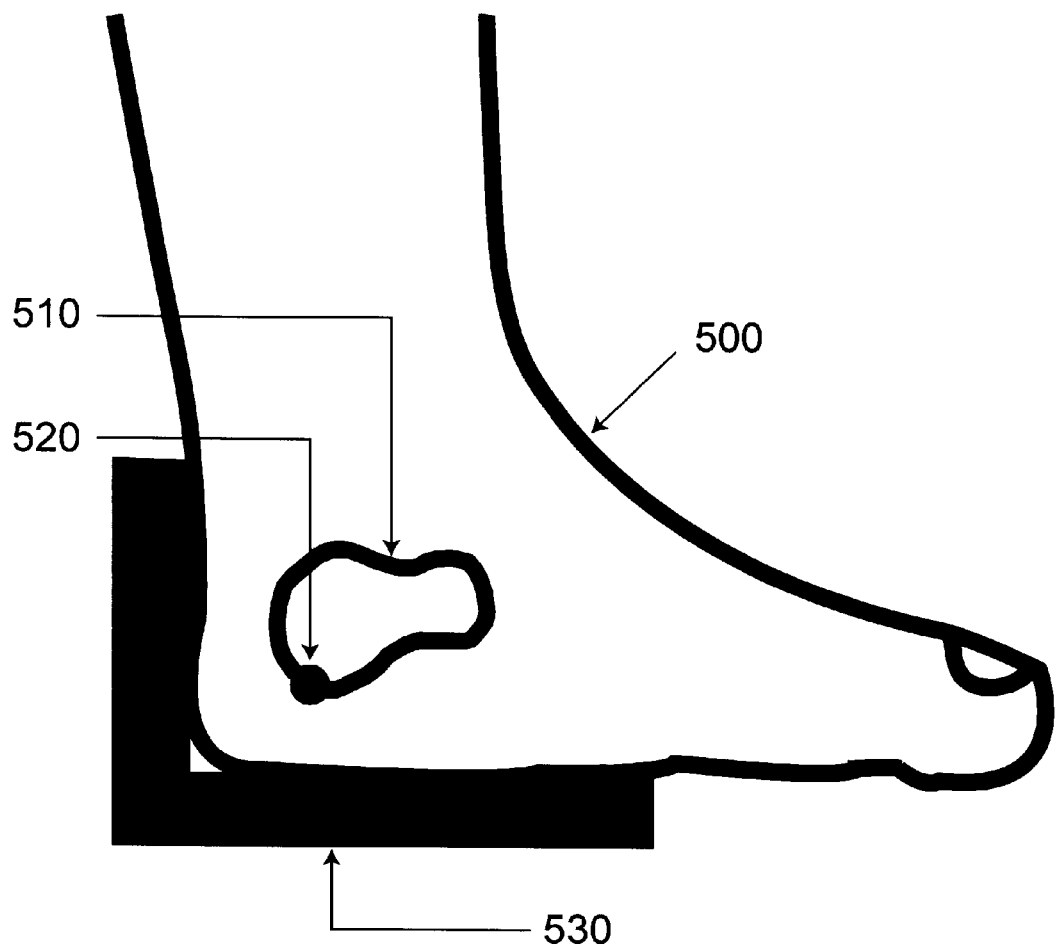
FIG. 5B shows an example of a typical prior art device for measuring the speed of sound or broadband ultrasonic attenuation in a patient with peripheral edema. Edema increases the thickness of the soft tissue inferior and posterior to the calcaneus. Since the position of the ultrasonic interrogation site 520 is fixed relative to the device frame 530, a more inferior and posterior region is measured within the calcaneus 510 when compared to FIG. 5A that is even partially outside the calcaneus 510.

FIG. 5B shows an example of a typical prior art device for measuring the speed of sound or broadband ultrasonic attenuation in a patient with peripheral edema. Edema increases the thickness of the soft tissue inferior and posterior to the calcaneus. Since the position of the ultrasonic interrogation site 520 is fixed relative to the device frame 530, a more inferior and posterior region is measured within the calcaneus 510 when compared to FIG. 5A that is even partially outside the calcaneus 510.

Figure 5C:
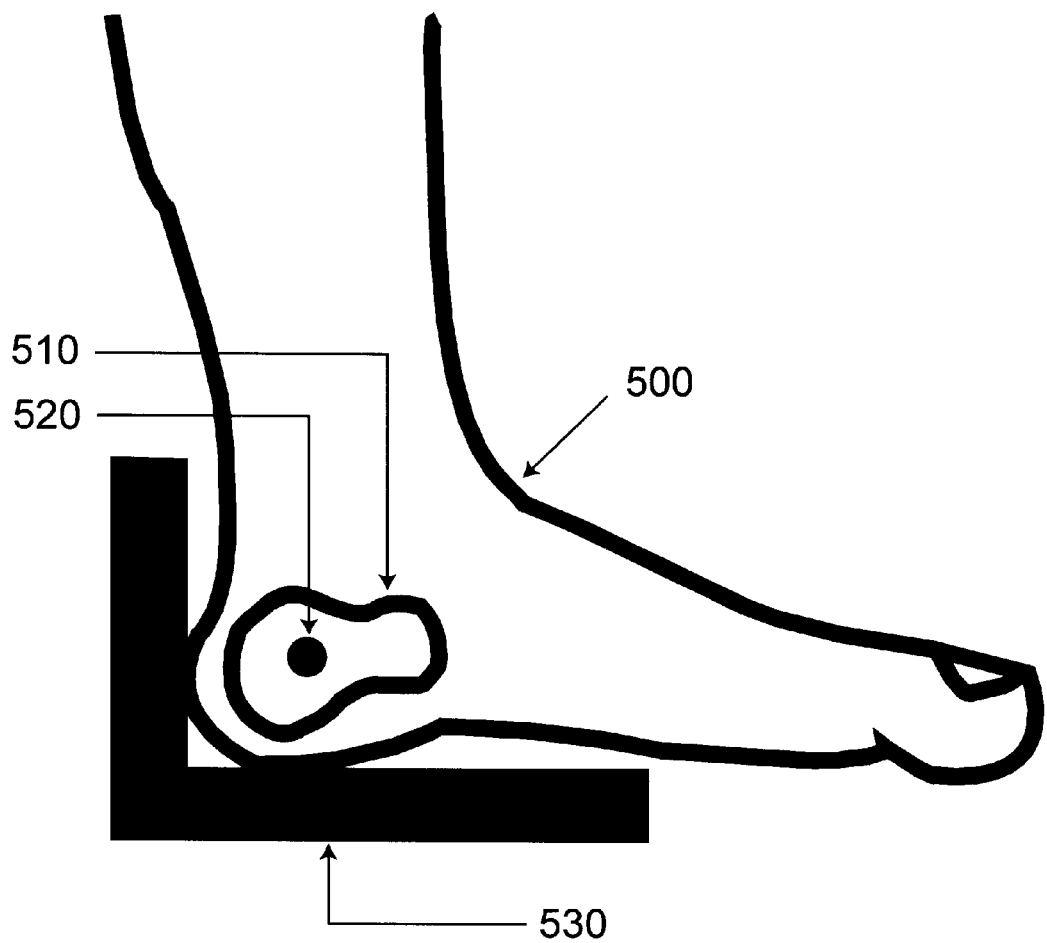
FIG. 5C shows one embodiment of the invention with a probe for measuring speed of sound or broadband ultrasonic attenuation of the calcaneus, in this case in a healthy non-edematous patient. The position of the ultrasonic interrogation site 520 is not fixed with respect to the device frame 530 but is determined, for example, based on landmarks or anatomical maps using A-scan or B-scan ultrasonics.

FIG. 5C shows one embodiment of the invention with a probe for measuring speed of sound or broadband ultrasonic attenuation of the calcaneus, in this case in a healthy non-edematous patient. The position of the ultrasonic interrogation site 520 is not fixed with respect to the device frame 530 but is determined, for example, based on landmarks or anatomical maps using A-scan or B-scan ultrasonics.

Figure 5D:
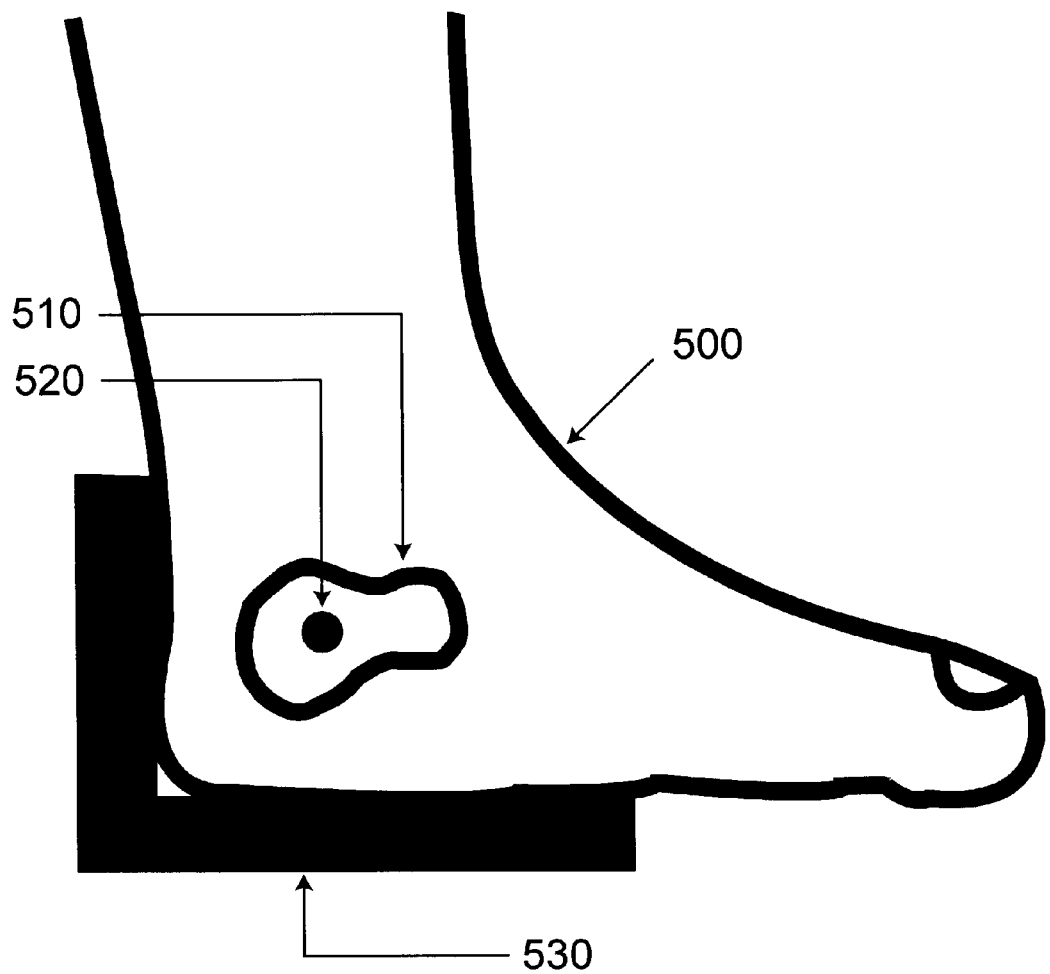
FIG. 5D shows the same embodiment of the invention as seen in FIG. 5C with a probe for measuring speed of sound or broadband ultrasonic attenuation of the calcaneus, in this case in a patient with peripheral edema. Edema increases the thickness of the soft tissue inferior and posterior to the calcaneus. Since the position of the ultrasonic interrogation site 520 is not fixed relative to the device frame 530, but is determined, for example, based on landmarks or anatomical maps using A-scan or B-scan ultrasonic, the interrogation site in the calcaneus remains substantially constant in the presence of peripheral edema and does not change significantly compared to conditions illustrated in FIG. 5C.

FIG. 5D shows the same embodiment of the invention as seen in FIG. 5C with a probe for measuring speed of sound or broadband ultrasonic attenuation of the calcaneus, in this case in a patient with peripheral edema. Edema increases the thickness of the soft tissue inferior and posterior to the calcaneus. Since the position of the ultrasonic interrogation site 520 is not fixed relative to the device frame 530, but is determined, for example, based on landmarks or anatomical maps using A-scan or B-scan ultrasonics, the interrogation site in the calcaneus remains substantially constant in the presence of peripheral edema and does not change significantly compared to conditions illustrated in FIG. 5C.

Figure 6A:
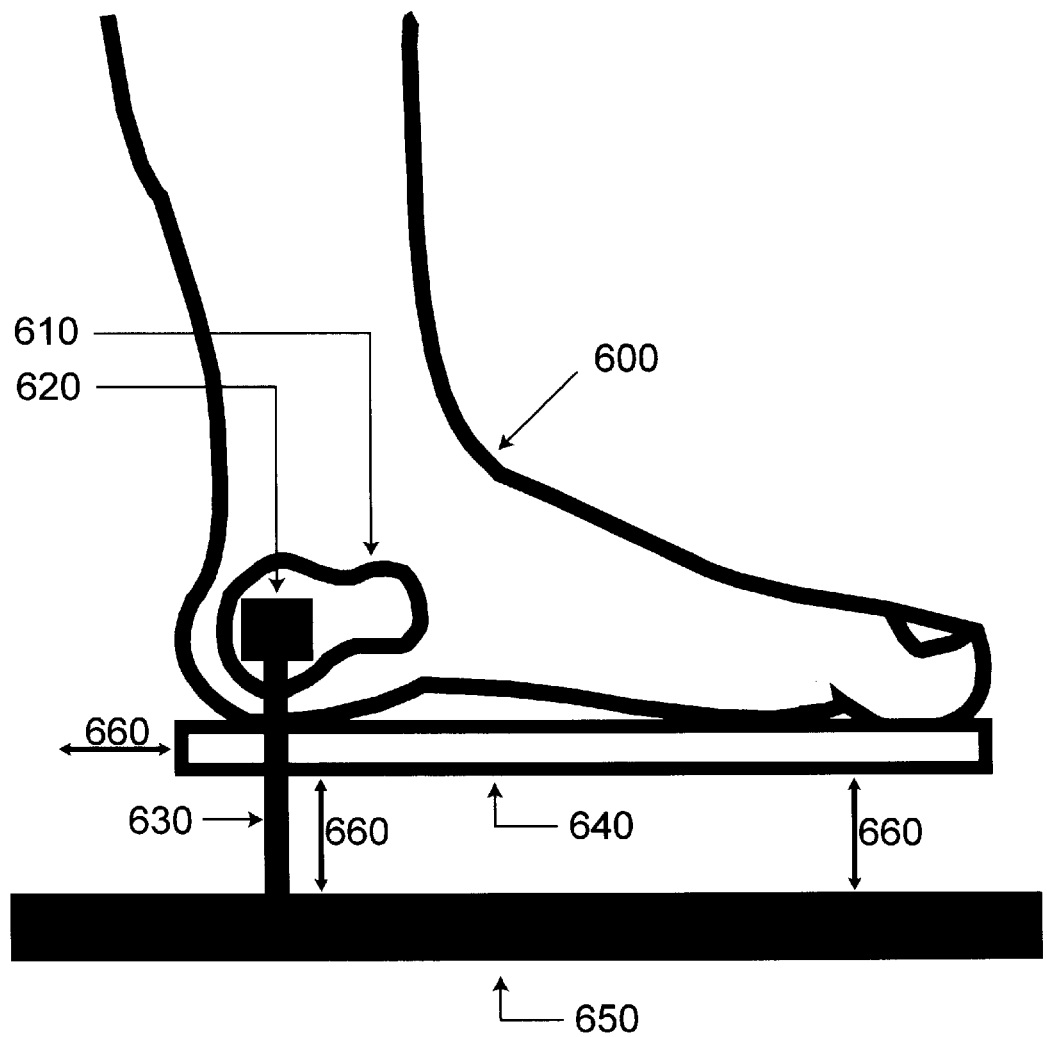
FIG. 6A shows another embodiment of the invention with a device for measuring speed of sound or broadband ultrasonic attenuation of the calcaneus, in this case in a healthy non-edematous patient. The position of the patient's foot 600 and of the calcaneus 610 are not fixed with respect to the device frame 650. The ultrasonic transducer 620 is, however, attached 630 to the device frame 650. The foot 600 is placed on a foot holder 640 that can be moved in the x- or y-direction 660. The foot 600 and the calcaneus 610 are positioned relative to the ultrasonic transducer 620 for example based on landmarks or anatomic maps using A-scan or B-scan ultrasonics.

FIG. 6A shows another embodiment of the invention with a device for measuring for example speed of sound or broadband ultrasonic attenuation of the calcaneus, in this case in a healthy non-edematous patient. The position of the patient's foot 600 and of the calcaneus 610 are not fixed with respect to the device frame 650. The ultrasonic transducer 620 is, however, attached 630 to the device frame 650. The foot 600 is placed on a foot holder 640 that can be moved in the x- or y-direction 660. The foot 600 and the calcaneus 610 are positioned relative to the ultrasonic transducer 620 for example based on landmarks or anatomic maps using A-scan or B-scan ultrasonics.

Figure 6B:
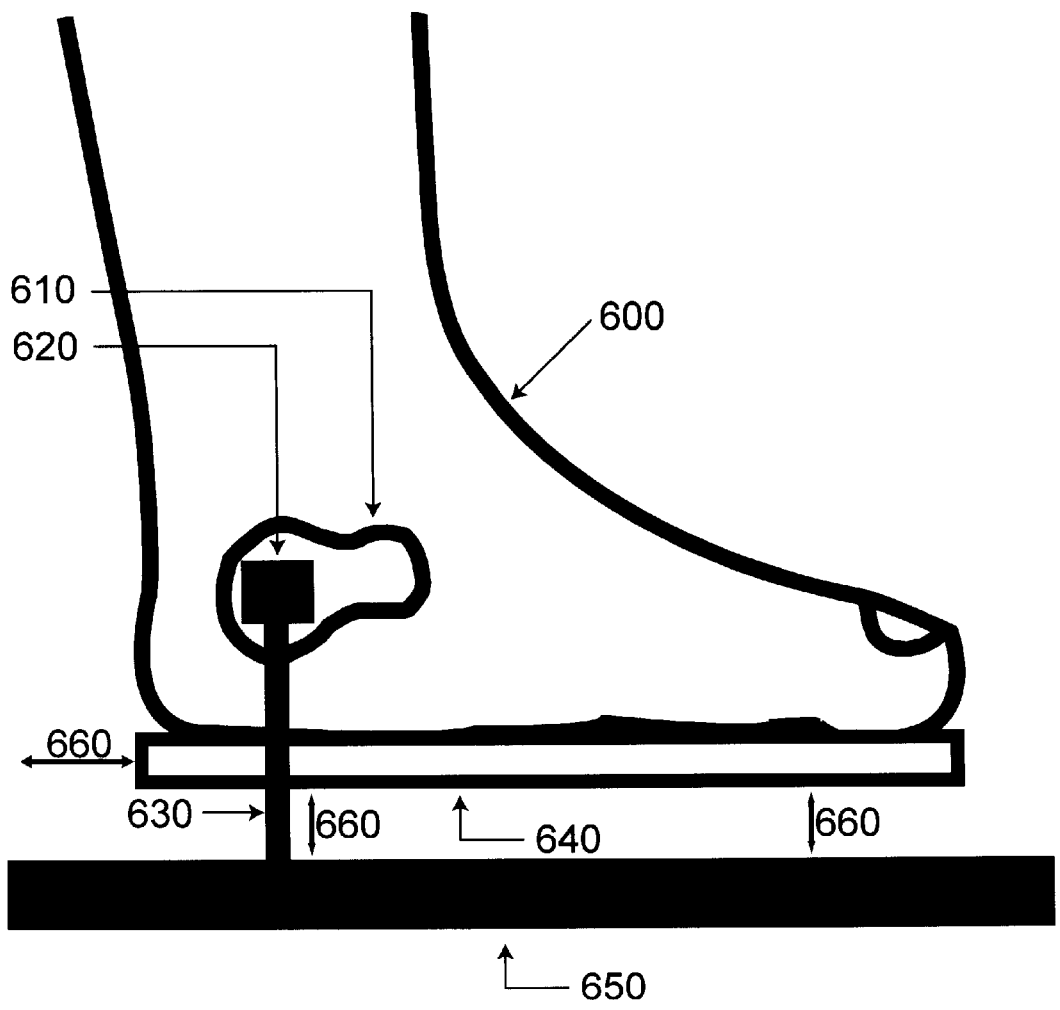
FIG. 6B shows the same embodiment of the invention as demonstrated in FIG. 6A with a probe for measuring speed of sound or broadband ultrasonic attenuation of the calcaneus, in this case in a patient with peripheral edema. Since the position of the foot 600 and of the calcaneus 610 is not fixed relative to the device frame 650, but is determined, for example, based on landmarks or anatomical maps using A-scan or B-scan ultrasonics, the interrogation site of the ultrasonic transducer 620 at the calcaneus remains substantially constant in the presence of peripheral edema and does not change significantly when compared to the condition illustrated in FIG. 6A. This type of device is preferred.

FIG. 6B shows the same embodiment of the invention as demonstrated in FIG. 6A with a probe for measuring for example speed of sound or broadband ultrasonic attenuation of the calcaneus, in this case in a patient with peripheral edema. Since the position of the foot 600 and of the calcaneus 610 is not fixed relative to the device frame 650, but is determined, for example, based on landmarks or anatomical maps using A-scan or B-scan ultrasonics, the interrogation site of the ultrasonic transducer 620 at the calcaneus remains substantially constant in the presence of peripheral edema and does not change significantly when compared to the condition illustrated in FIG. 6A.

Many of the positioning embodiments of the invention can be used to assist in enhancing such measurements and as described further herein anatomical landmarks can also be used to enhance measurements.

For example, in one embodiment an A-scan or B-scan ultrasonic device is used to identify a contour or landmarks of the calcaneus. Specifically, the posterior and inferior margin or other bony landmarks of the calcaneus are detected and registered spatially, e.g. on a coordinate system in the system computer. The transducer(s) for BUA and SOS measurements are subsequently positioned using the bone margins or landmarks (inferior and posterior or other) as reference points or using the coordinate system. On follow-up examinations in the same patient, the system will automatically or using operator assistance find the same bony margins/landmarks and position the transducer(s) over the same measurement site(s) of the calcaneus that was evaluated during the previous examination(s). This type of positioning ensures reproducible placement of the transducer(s) over the same measurement area of the calcaneus. In-vivo reproducibility of SOS and BUA will be markedly improved using this technique.

The invention also includes an ultrasonic method for generating an anatomic landmark in the heel for ultrasonic interrogation for BUA or SOS measurements, comprising:

a) positioning, with respect to an anatomical region of a heel, an ultrasonic transducer unit comprising a pair of ultrasonic transducers where a first member of the pair is designed to transmit signals and a second member of the pair is designed to receive signals, and b) interrogating the anatomical region with the ultrasonic transducer unit, and c) identifying an anatomic landmark in the anatomical region with an ultrasonic property of the anatomical region, and d) optionally storing the anatomic landmark in a storage device.

The ultrasonic method can further comprise the steps of comparing the location of the ultrasonic transducer unit to the location of the anatomic landmark and positioning the ultrasonic transducer unit to produce an axis of transmission generally through the anatomic landmark. Steps a, b, and c can be optionally repeated. This can increase accuracy or permit close matching of observed landmarks with reference maps or landmarks. Each positioning step can be performed in relation to an anatomic landmark. The positioning steps are typically performed to generate an axis of transmission substantially through the anatomic landmark. Although the transmission axis can be in a predetermined coordinate or desired spatial relationship with respect to the landmark. The positioning steps can be performed to in relation to a reference anatomic landmark of the anatomical region that is stored in retrievable form on a storage device.

EXAMPLES

The following materials and methods are exemplary of the materials and methods that can be used to achieve the results described herein. These examples are for illustrative purposes only, and are not to be construed as limiting the appended claims. One skilled in the art will readily recognize substitute materials and methods.

General Materials and Methods

In vivo ultrasonic measurements are performed using a prototype ultrasonic system capable of measuring speed of sound and broadband ultrasonic attenuation in the heel region in addition to A-scan measurements.

The ultrasonic system consists of two ultrasonic sources mounted on a U-shaped plastic frame. A hinge is located in the center portion of the U-shaped plastic frame that allows for adjusting the distance between the ultrasonic transducers for each individual patient. The physical distance separating both transducers is registered for each patient using an electronic system that employs a potentiometer. The U-shaped plastic frame is connected to a plastic housing on which the patient can rest the fore- and mid-foot and in particular the heel comfortably. The ultrasonic sources are placed by the operator on the left and the right side of the foot in the heel region. An ultrasonic gel is used for acoustic coupling. The operator adjusts the frame and the attached ultrasonic sources visually so that they are flush with the skin and near perpendicular to the skin surface.

The ultrasonic system is designed with a central processing unit responsible for pulsing the ultrasonic transducer(s) and crystal(s), registering signals returned from the transducer, preamplification of the electronic signal, time gain compensation, signal compression, signal rectification, demodulation, and envelope detection, signal rejection, signal processing, analysis and display of SOS, BUA, and soft tissue and bone distance measurements. Transducers operate at a center frequency of 1 Mhz. However, transducer center frequency can be switched from 1 to 0.5 MHz. As the interrogation frequency of the micro-transducer decreases, generally, the ability to resolve reflective surfaces at deeper depths improves. The lower frequency is used in obese or edematous patients in whom tissue penetration with the 1 MHz probe is insufficient.

With each measurement the device registers initially the physical distance between both transducers. The device then measures (a) speed of sound, and (b) broadband ultrasonic attenuation in the heel. Broadband ultrasonic attenuation is calculated by subtracting the amplitude spectrum of a patient from one obtained in a reference material (e.g. de-gassed water).

As an alternative, ultrasonic measurements can also be performed using another prototype system that is capable of two-dimensional image acquisition and display using B-scan technology in addition to SOS and BUA measurements. This ultrasonic system also uses two or more ultrasonic sources mounted on a hinged, U-shaped plastic frame. The physical distance separating both transducers is registered for each patient using an electronic system. After positioning of the patient and the transducers and application of the acoustic coupling gel, data are acquired in B-scan mode. Two-dimensional gray-scale images of the various tissues are obtained. Images are displayed on a computer monitor attached to the scanner hardware.

All experiments performed on human subjects shall be performed with the highest ethical and medical standards and in accordance with the relevant laws, guidelines and regulations of the relevant governing jurisdiction(s) or professional association(s), including, where appropriate, compliance under 45 CFR 46 relating to United States federal policy for the protection of human subjects.

Example 1

Correction for Edema-Induced Changes in Ultrasonic Probe Position

This example shows among other things that the presence of peripheral edema affects ultrasonic probe position relative to the underlying bone. This examples documents that edema induced changes in ultrasonic probe position over the calcaneus and general variations in ultrasonic probe position over the calcaneus reduce short-term and long-term in vivo precision of SOS and BUA measurements.

Twenty patients with compromised cardiac performance and peripheral edema are selected for the study. SOS and BUA measurements are performed at different times in the day on two different days: In the morning on day 1 before 9 am and in the evening on day 2 after 6 pm. At each time interval, the degree of peripheral edema is assessed clinically by visual inspection and manual palpation. Using standard clinical techniques (see Bates et at., J. B. Lippincott, 1995), edema is subdivided into 5 grades:

0.) absent,
1.) slight,
2.) mild,
3.) moderate, and
4.) severe.

Ultrasonic measurements are performed in each patient using a conventional ultrasonic system that is capable of SOS and BUA measurements (Sahara™, Hologic Inc., Waltham, Mass. 02154). With this system, the position of the patient's foot and calcaneus is fixed with respect to the device frame and the transducers. The patient's foot is secured in the ultrasonic device so that the heel of the foot rests on the heel pad of the device and the posterior aspect of the heel touches the back-wall of the instrument (see also FIGS. 5A and 5B). A small amount of acoustic coupling gel is applied to the skin and the ultrasonic transducers are placed against the skin at the measurement site.

SOS and BUA measurements are then repeated using a second, different, prototype ultrasonic system. This second system is capable of identifying the posterior contour and the inferior contour, i.e. the bright, echogenic cortex, of the calcaneus on the B-scan images. Using these landmarks, the system positions the ultrasonic transducers automatically over a predefined region in the calcaneus, e.g. 1.5 cm anterior to the posterior calcaneal cortex and 1.5 cm superior to the inferior calcaneal cortex. In this fashion, the ultrasonic transducers are reproducibly positioned over the same measurement site in the calcaneus regardless of changes in the thickness of the posterior and inferior heel soft tissue pad (see also FIGS. 5C and 5D).

In-vivo reproducibility between am and pm measurements is better with the second ultrasonic system that adjusts probe position relative to the posterior and the inferior cortex of the calcaneus than with the conventional system with fixed probe position relative to skin/patient/heel surface.

Example 2

Correction for Edema-Induced Changes in Ultrasonic Probe Position and Its Influence on In-Vivo Reproducibility of Calcaneal Speed of Sound and Broadband Ultrasonic Attenuation before and after Diuretic Therapy The experimental design used in this example is identical to that shown in Example 1. However, rather than assessing the influence of diurnal changes in tissue edema between morning and evening measurements, twenty patients with compromised cardiac performance and peripheral edema are studied prior to and two weeks after initiation of diuretic therapy.

The results show that in-vivo reproducibility of SOS and BUA is better when the ultrasonic system is capable of adjusting probe position relative to the anatomic landmarks, e.g. posterior and inferior cortex, of the calcaneus than with an ultrasonic system where the probe position is fixed relative to skin/patient/heel surface.

PUBLICATIONS

U.S. PATENT DOCUMENTS

| | | |
|---|---|---|
| 3,648,685 | Mar. 14, 1972 | Hepp, J. A., et al. |
| 3,713,329 | Jan. 30, 1973 | Munger, D. W. |
| 3,782,177 | Jan. 1, 1974 | Hoop, J. M. |
| 3,847,141 | Nov. 12, 1974 | Hoop, J. M. |
| 4,043,181 | Aug. 23, 1977 | Nigam, A. K. |
| 4,048,986 | Sep. 20, 1977 | Ott, J. H. |
| 4,056,970 | Nov. 8, 1977 | Sollish, B. D. |
| 4,224,829 | Sep. 30, 1980 | Kawabuchi, M., et al. |
| 4,235,243 | Nov. 25, 1980 | Saha, S. |
| 4,242,911 | Jan. 6, 1981 | Martin, R. E. |
| 4,361,154 | Nov. 30, 1982 | Pratt, G. W. |
| 4,421,119 | Dec. 20, 1983 | Pratt, G. W. |
| 4,446,737 | May 8, 1984 | Hottier, F. |
| 4,522,068 | Jun. 11, 1985 | Smith, G. E. |
| 4,530,360 | Jul. 23, 1985 | Duarte, L. R. |
| 4,658,827 | Dec. 21, 1987 | He, P., et al. |
| 4,688,428 | Aug. 25, 1987 | Nicolas, J. -M. |
| 4,702,258 | Oct. 27, 1987 | Nicolas, J. -M., et al. |
| 4,774,959 | Oct. 4, 1988 | Palmer, S. B., et al. |
| 4,830,015 | May 16, 1989 | Okazaki, K. |
| 4,913,157 | Apr. 3, 1990 | Pratt, G. W., et al. |
| 4,930,511 | Jun. 5, 1990 | Rossman, P. J., et al. |
| 5,042,489 | Aug. 27, 1991 | Wiener, S. A., et al. |
| 5,054,490 | Oct. 8, 1991 | Rossman, P. J., et al. |
| 5,099,849 | Mar. 31, 1992 | Rossman, P. J., et al. |
| 5,119,820 | Jun. 9, 1992 | Rossman, P. J., et al. |
| 5,218,963 | Jun. 15, 1993 | Mazess, R. B. |
| 5,271,403 | Dec. 21, 1993 | Paulos, J. J. |
| 5,343,863 | Sep. 6, 1994 | Wiener, S. A., et al. |
| 5,349,959 | Sep. 27, 1994 | Wiener, S. A., et al. |
| 5,452,722 | Sep. 26, 1995 | Langton, C. M. |
| 5,483,965 | Jan. 16, 1996 | Wiener, S. A., et al. |
| 5,603,325 | Feb. 18, 1997 | Mazess, R. B., et al. |
| 5,649,538 | Jul. 22, 1997 | Langton, C. M. |

FOREIGN PATENT DOCUMENTS

WO 80/02796 Jun. 9, 1980 Pratt, G.

OTHER PUBLICATIONS

Agren, M., et al., Calc Tiss Int, vol. 48, pp. 240–244, 1991.
Bates, B., et al., in: "A guide to physical examination and history taking, 6th edition", Bates, B., et al., eds., pp.427–447, 1995.
Biot, M. A., J Acoust Soc Am, vol. 34, pp. 1254–1264, 1962.
Bradenburger, G., et al., J Bone Miner Res, vol. suppl. 1, pp. S184, 1992.
Dretakis, E., et al., Br J Radiol, vol. 67, pp. 636–638, 1994.
Faulkner, K. G., et al., Am J Roentgenol, vol. 157, pp. 1229–37, 1991.
Gluer, C. C., et al., J Bone Min Res, vol. 7 (9), pp. 1071–1079, 1992.
Gluer, C. C., et al., Calc Tiss Int, vol. 55, pp. 46–52, 1994.
Goss, S. A., et al., J Acoust Soc Am, vol. 64 (2), pp. 423–457, 1978.
Greespan, M., et al., J Acoust Soc Am, vol. 31, pp. 75–76, 1959.
Hans, D., et al., Bone, vol. 16, pp. 476–480, 1995.
Lang, P., et al., Radiol Clin North Am, vol. 29, pp. 49–76, 1991.
Langton, C. M., et al., Bone, vol. 18, 6, pp. 495–503, 1996.
Langton, C. M., et al., Eng Med, vol. 13, pp. 89–91, 1984.
McCloskey, E. V., et al., Clin Sci, vol. 78, pp. 221–227, 1990.
Njeh, C. F., et al., Med Eng Phys, vol. 18, pp. 373–381, 1996.
Rossman, P. J., et al., Clin Phys Physiol Meas, vol. 10, pp.353–360, 1989.
Schott, A. M., et al., Osteoporosis Int, vol. 3, pp. 249–254, 1993.
Turner, C. H., et al., Calc Tiss Int, vol. 49, pp. 116–119, 1991.
Williams, J. L., J Acoust Soc Am, vol. 91, pp. 1106–1112, 1992.
Williams, P., et al. "Gray's anatomy, 36th British Edition", 1980.
Zagzebski, J. A., et al., Calc Tiss Int, vol. 49, pp. 107–111, 1991.

All documents and publications, including patents and patent application documents, are herein incorporated by reference to the same extent as if each publication were individually incorporated by reference.

We claim:

1. An ultrasonic system for automated ultrasonic identification of an anatomical landmark for BUA and SOS measurements in the heel, comprising:

a) an ultrasonic transducer unit comprising:

1) a pair of ultrasonic transducers adapted for BUA or SOS measurements or both, wherein a first member of said pair is designed to transmit signals and a second member of said pair is designed to receive signals, and 2) said ultrasonic transducer unit includes a transducer adapted for either A-scan or B-scan or both to identify an anatomical landmark; and b) a computational unit designed 1) to manage ultrasonic signal transmission and reception of said ultrasonic transducer unit, including, transmission and reception from said pair of ultrasonic transducers adapted for BUA or SOS measurements or both and said transducer adapted for either A-scan or B-scan or both; and 2) to process signals to identify an anatomical landmark in an anatomical region of the heel in either a A-scan or B-scan mode or both from said transducer adapted for either A-scan or B-scan or both;

wherein said computational unit and said ultrasonic transducer unit are coupled to permit transfer of signals between said computational unit and said ultrasonic transducer unit.

2. The ultrasonic system of claim 1, wherein said computational unit is designed to process ultrasonic signals received from said ultrasonic transducer unit to generate an anatomical map using either signals from A-scan or B-scan or both from said anatomical region and said anatomical map can provide coordinates to locate said anatomical landmark within said anatomical region of the heel.

3. The ultrasonic system of claim 2, wherein said computational unit is further designed to process received ultrasonic signals from said ultrasonic transducer unit to generate at least one data set of an ultrasonic property and to generate said anatomical map from at least a portion of said data set.

4. The ultrasonic system of claim 3, wherein said ultrasonic property is determined from said transducer adapted for either A-scan or B-scan or both and is selected from the group consisting of echogenicity, distances from said transducer unit, and ultrasonic images.

5. The ultrasonic system of claim 4, wherein said computational unit further comprises a database comprising at least one reference anatomical map and said computational unit is further designed to compare said anatomical map with said reference anatomical map.

6. The ultrasonic system of claim 2, wherein said ultrasonic system further comprises a positioning unit for changing the spatial relationship between said anatomical landmark in said anatomical region of the heel and said ultrasonic transducer unit, thereby permitting interrogation with reference to said anatomical landmark in said anatomical region of the heel by positioning said ultrasonic transducer unit with respect to said anatomical landmark.

7. The ultrasonic system of claim 6, wherein said positioning unit positions said transducer unit with respect to said anatomical landmark.

8. The ultrasonic system of claim 7, wherein said positioning unit is controlled by said computational unit based B-scan signals.

9. The ultrasonic system of claim 6, wherein said anatomical map is based on signals from said transducer and said transducer is made of ultrasonic crystals arranged in an array.

10. An ultrasonic system for tissue ultrasonic interrogation for broadband ultrasonic attenuation or speed of sound in a heel, comprising:

a) transmission-reception unit, comprising:
i) a first ultrasonic transducer with a first axis of transmission through a first anatomical region to be interrogated and said first ultrasonic transducer is adapted for BUA or SOS measurements, and
ii) a second ultrasonic transducer with a second axis of transmission through a second anatomical region to be interrogated and adapted for BUA or SOS measurements, wherein said first anatomical region and said second anatomical region permit monitoring broadband ultrasonic attenuation or speed of sound between said first ultrasonic transducer and said second ultrasonic transducer, b) a positioning unit to automatically position said first ultrasonic transducer with respect to said first anatomical region and to position said second ultrasonic transducer with respect to said second anatomical region in the x, y, and z-dimensions, and c) a computational unit designed to manage ultrasonic signal transmission of said first ultrasonic transducer, to manage ultrasonic signal reception of said second ultrasonic transducer and to control said positioning unit and identify an anatomical landmark.

11. The ultrasonic system of claim 10, wherein said positioning unit comprises an x, y positioner for said first ultrasonic transducer and said second ultrasonic transducer that can position within about plus or minus 3 mm.

12. The ultrasonic system of claim 11, wherein said x, y positioner is designed to simultaneously position said first ultrasonic transducer and said second ultrasonic transducer by computer control, wherein said first axis of transmission generally has the same axis of transmission as said second axis of transmission and said x, y positioner positions said first ultrasonic transducer and said second ultrasonic transducer based on an anatomical landmark identified with A-scan or B-scan signals or both.

13. The ultrasonic system of claim 10, wherein said computational unit comprises a program to generate an anatomical landmark to assist in reproducible positioning of said first ultrasonic transducer and said second ultrasonic transducer and said positioning unit comprises a z positioner controlled by said computational unit to separately position the said first ultrasonic transducer and said second ultrasonic transducer.

14. The ultrasonic system of claim 10, wherein said first ultrasonic transducer and said second ultrasonic transducer are tandem transducers.

15. The ultrasonic system of claim 10, wherein said computational unit can identify an anatomical landmark in an interrogated tissue less than about 1 $cm^2$ and direct said x, y positioner to a position over said anatomical landmark thereby said first ultrasonic transducer and second ultrasonic transducer have an axis of transmission generally through said anatomical landmark.

16. The ultrasonic system of claim 1, wherein said computational unit further comprises instructions to direct a positioning unit to position said transducer unit with reference to said anatomical landmark.

17. The ultrasonic system of claim 16, wherein said computational unit is designed to instruct said transducer unit to transmit and receive signals after positioning said transducer unit with respect to said anatomical landmark and said anatomical landmark is less than 1 $cm^2$.

18. The ultrasonic system of claim 17, wherein said computational unit further comprises a display for showing said anatomical map or said anatomical landmark.

19. An ultrasonic method for generating an anatomical landmark for BUA or SOS measurement in the heel of a human in need of diagnosis of osteoporosis, comprising:

a) positioning, with respect to an anatomical region of the heel, an ultrasonic transducer unit comprising a pair of ultrasonic transducers where a first member of said pair is designed to transmit signals and a second member of said pair is designed to receive signals from said first member, b) interrogating said anatomical region with said ultrasonic transducer unit and c) identitying, an anatomical landmark about 2 cm² or less in said anatomical region with an ultrasonic property of said anatomical region of the heel selected from the group of an A-scan data, a B-scan data and a combination of A-scan data and B-scan data, and d) storin said anatomical landmark in a storage device.

20. The ultrasonic method of claim 19, further comprising the steps of comparing the location of said ultrasonic transducer unit to the location of said anatomical landmark and positioning said ultrasonic transducer unit to produce an axis of transmission at a preselected or desired set of coordinates in relation to said anatomical landmark of the heel.

21. The ultrasonic method of claim 20, wherein steps a, b, and c are repeated and each positioning step is performed in relation to said anatomical landmark and said ultrasonic transducer unit is comprised of a tandem transducer.

22. The ultrasonic method of claim 21, wherein said positioning steps are performed to generate an axis of transmission substantially through said anatomical landmark.

23. The ultrasonic method of claim 22, wherein said positioning steps are performed to in relation to a reference anatomical landmark of said anatomical region stored in retrievable form in a storage device.

24. A computer program product, comprising:

a) instructions for a positioning unit to position a transducer unit at a plurality of interrogation sites in an anatomical region of a heel, b) instructions for interrogating said anatomical region with said transducer unit at said plurality of interrogation sites, c) instructions for generating a map of said anatomical region using ultrasonic measurements based on A scan or B scan data or a combination thereof from said plurality of interrogation sites, d) instructions for said positioning unit to position said transducer or said plurality of transducers at a second plurality of interrogation sites in said anatomical region if said map lacks sufficient features to be clinically relevant for a clinically relevant BUA or SOS measurement, e) instructions for interrogating said anatomical region for a clinically relevant BUA and SOS measurement;

wherein instructions (a) through (e) permit the generation of said map which facilitates a clinically relevant BUA or SOS measurement and instructions (a) through (e) are stored on a computer retrievable medium.

25. The computer program product of claim 24, further comprising:

i) instructions for comparing said map with a reference map of substantially the same anatomical region using predefined criteria, said predefined criteria optionally comprising percent similarity of contours of bones, percent similarity of an anatomical landmark or percent similarity of reflective surfaces, j) instructions for interrogating said anatomical region for a clinically relevant BUA or SOS measurement if said map matches said reference map, and k) instructions for said positioning unit to position said transducer unit at a second plurality of interrogation sites in said anatomical region if said map lacks sufficient features to be clinically relevant for a clinically relevant BUA or SOS measurement.

26. The computer program product of claim 24, wherein the computer program includes instructions for generating said map based on B-scan data.

* * * * *